United States Patent [19]
Wells et al.

[11] Patent Number: 5,355,212
[45] Date of Patent: Oct. 11, 1994

[54] PROCESS FOR INSPECTING PATTERNED WAFERS

[75] Inventors: Keith B. Wells, Santa Cruz; Hung Nguyen, Santa Clara; Ralph T. Johnson, Los Gatos; Brian C. Leslie, Cupertino, all of Calif.

[73] Assignee: Tencor Instruments, Mountain View, Calif.

[21] Appl. No.: 93,999

[22] Filed: Jul. 19, 1993

[51] Int. Cl.⁵ ............................................. G01N 21/88
[52] U.S. Cl. ...................................... 356/237; 356/394
[58] Field of Search ................................. 356/237, 394

[56] References Cited

U.S. PATENT DOCUMENTS

| | | | |
|---|---|---|---|
| 4,641,967 | 2/1987 | Pecen | 356/237 |
| 4,898,471 | 2/1990 | Stonestrom et al. | 356/394 |
| 5,076,692 | 12/1991 | Neukermans et al. | 356/538 |
| 5,189,481 | 2/1993 | Jann et al. | 356/73 |

Primary Examiner—Vincent P. McGraw
Attorney, Agent, or Firm—Schneck & McHugh

[57] ABSTRACT

A method of locating particle and defect features on a periodically patterned surface uses multiple threshold intensity levels to identify features in the data stream produced by scanning the surface with a light beam and detecting the light scattered from the surface. High thresholds are assigned to regions of the surface with high background scatter, while low thresholds are assigned to regions of the surface with low background scatter. The scattered light is detected with a wide dynamic range detector producing high resolution 12-bit pixel data capable of resolving the smallest particles and defects of interest in low scatter regions, while avoiding saturation in high scatter regions. Periodic pattern features are removed from the data by mapping features from a plurality of periodically repeating die on the surface to a single die map and looking for overlapping features. Unique, nonoverlapping features are determined to correspond to particles and defects. In one embodiment, only a portion of all the die on the surface are mapped at one time to reduce the possibility of accidental overlap of particle and defect features.

29 Claims, 6 Drawing Sheets

PROCESS FOR INSPECTING PATTERNED WAFERS

TECHNICAL FIELD

The present invention relates to surface inspection systems measuring optical scattering of a scanning beam by surface features, including pattern features, surface defects and particles, on a patterned wafer, and in particular relates to data processing methods for eliminating pattern features from the scattering data to locate the particles and defects on the surface.

BACKGROUND ART

In U.S. Pat. No. 4,898,471, Stonestrom et al. describe a method of particle detection on a periodic patterned surface. A light collection system for collecting light scattered from the surface is arranged to maximize the particle signal compared to the pattern signal. A detector produces an electrical signal corresponding to the intensity of scattered light that is collected. A processor constructs wave form templates from the electrical signal corresponding to individual die on the surface and compares the templates to identify particles. Differences between the templates represent particles on the surface in the scan path. The reference template may be made up of registered positions of features where the detected scattering signal exceeds a preselected threshold value, so that the comparison is between corresponding positions to eliminate periodic pattern features, leaving only positions representing particles. The reference template can be constantly updated to the just compared template after each comparison, provided no particle is found, so that comparisons are mainly between adjacent die.

Such a method has been found to be useful for inspecting patterned surfaces where a relatively low particle or defect density is expected, provided the pattern on the surface generally has a single main background scattering intensity. Areas of the wafer surface where the background scattering intensity is high cannot be inspected in the same scan as the other areas and in many cases cannot be inspected at all because of saturation of the detector and because a suitable threshold cannot be found to allow inspection of the high scattering areas at the same time that inspection for very small particles and defects in the principal areas is carried out. Further difficulties occur when the particle and defect density becomes relatively large.

An object of the present invention is to provide a data processing method for eliminating the pattern features from the scattering data obtained from inspecting a patterned surface for the entire surface without also eliminating a significant number of particle and defect features from the data and while permitting inspection of high scatter regions of the surface at the same time as low scatter regions.

DISCLOSURE OF THE INVENTION

The object is met with a method of detecting particles and defects on a periodically patterned surface which uses multiple thresholds, assigning higher threshold levels to regions of the surface with a higher background scattering intensity than the threshold levels assigned to regions with a lower scattering background. The method is therefore able to identify features of potential interest in the detected scattering signal in both high and low scatter regions with just a single scan of the surface. The method also uses a wide dynamic range detector, converting the analog scattering signal into a high resolution digital data stream, preferably 12-bits, provides enough discrete intensity levels (4096 levels using 12-bit pixels) to enable the smallest features of interest to be resolved in the data stream against background scattering, while also preventing saturation of high scattering levels. In a preferred embodiment, the 12-bit data stream can be nonlinearly transformed into 8-bit pixels by a transform converter executing a specified transform function, while still preserving resolution of the features of interest. After identifying features that are above the assigned threshold level for the respective scanned regions, their locations are compared to remove features that periodically recur. This can be done by mapping features for a plurality of periodically repeating die on the surface to a single die map such that feature positions relative to die on the surface correspond to map positions on the die map, and then identifying overlapping features on the die map as periodic pattern features. Unique (non-overlapping) features on the map are identified as randomly occurring particle and pattern features. Preferably, the mapping is done for features from only a portion of the surface at a time to minimize accidental overlaps of particle and pattern features.

BEST MODE OF CARRYING OUT THE INVENTION

Figure 1:
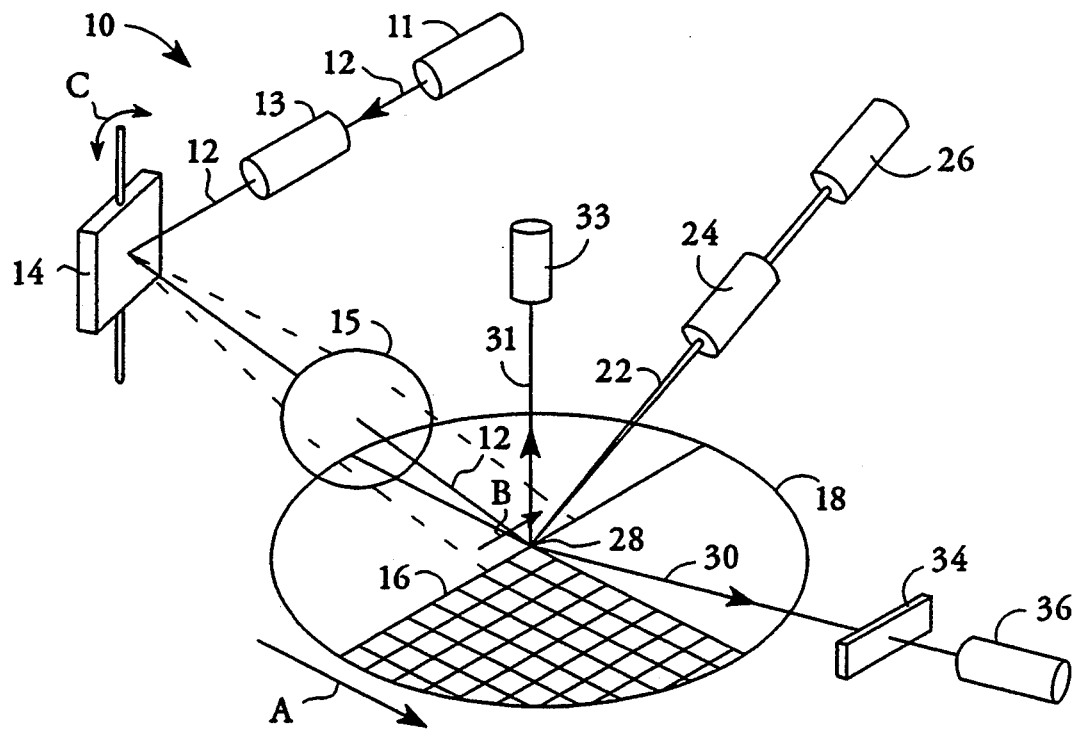
FIG. 1 is a perspective view of a surface inspection system for use with the data processing methods of the present invention.

With reference to FIG. 1, a surface inspection system 10 making use of the data processing methods of the present invention includes a beam source, such as a laser 11, directing a light beam 12 through a beam expander 13 toward a beam scanning mechanism 14, such as a rotating or oscillating mirror or prism, and from there through telecentric focusing optics 15 onto the surface 16 of a semiconductor wafer 18 or other generally flat object whose surface is to be inspected for particles or other defects on the surface. The wafer 18 may be moved by a transport mechanism (not shown) in a direction A perpendicular to the scan direction B of the beam 12 to cause the beam to sweep over the surface 16 in a series of adjacent, possibly overlapping, scan lines. The incident light 12 is scattered by any particles or surface defects, as well as by pattern features formed on the wafer 18. It is a particular object of the invention to provide improved data processing techniques for separating the random particles and defects from the essentially periodic pattern features and thereby provide more accurate information, e.g., number, location and size, about the particles and defects on the surface being inspected. The scattered light 22 is collected by light collection optics 24 and directed to a photodetector 26, such as a photomultiplier tube, for conversion into an electrical signal that corresponds to the detected intensity of the collected light. For example, one type of light collector 24 which may be used includes narrow aperture collection optics positioned to reduce collection of light scattered from pattern features relative to light scattered from particles and other defects. Typical narrow aperture light collectors are described in U.S. Pat. Nos. 4,898,471 to Stonestrom et al. and 5,076,692 to Neukermans et al. Light 31 scattered in a mainly vertical direction may be detected by another photodetector 33 and used to directly observe pattern features on the wafer 18.

Light 30 specularly reflected from the surface is not collected by the scattered light collection optics 24. Normally, the reflected light beam 30 would be sent to a beam dump and not used. However, it can be used to measure the thickness of thin films on the wafer surface 16 based on the polarization of the reflected light. A rotating polarizer 34 may be placed in the reflected beam path in front of a detector 36 that measures intensity for various polarizer orientations and produces a corresponding electrical signal. After being converted to digital form, the information is transmitted to a processor, such as a computer, which derives the elliptical polarization parameters $\phi$ and $\psi$ from the intensity measurements and then derives a measure of the thin film thickness at different locations on the wafer 18. Such derivations are well known in the art and have been used in commercially available thin film thickness measuring equipment. In addition to providing a measure of film thickness uniformity across the wafer, using the same apparatus and the same scan laser as that used simultaneously for particle/defect detection, the film thickness measurement can also be used to correct particle size measurements obtained from the particle detection process. Once particles have been detected and identified with the data processing methods described below, it is usually desirable to obtain a measure of their sizes for display in a histogram and for analysis. It is known that where particle size estimates are based either wholly or in part on scattering intensity, the thickness of the underlying thin film can affect the measurement, so that particles may look bigger or smaller than their actual sizes depending on the thin film thickness. The processor can use the film thickness measurements obtained from the reflected light 30 to correct the measurement of particle sized obtained from the scattered light 22.

Figure 2:
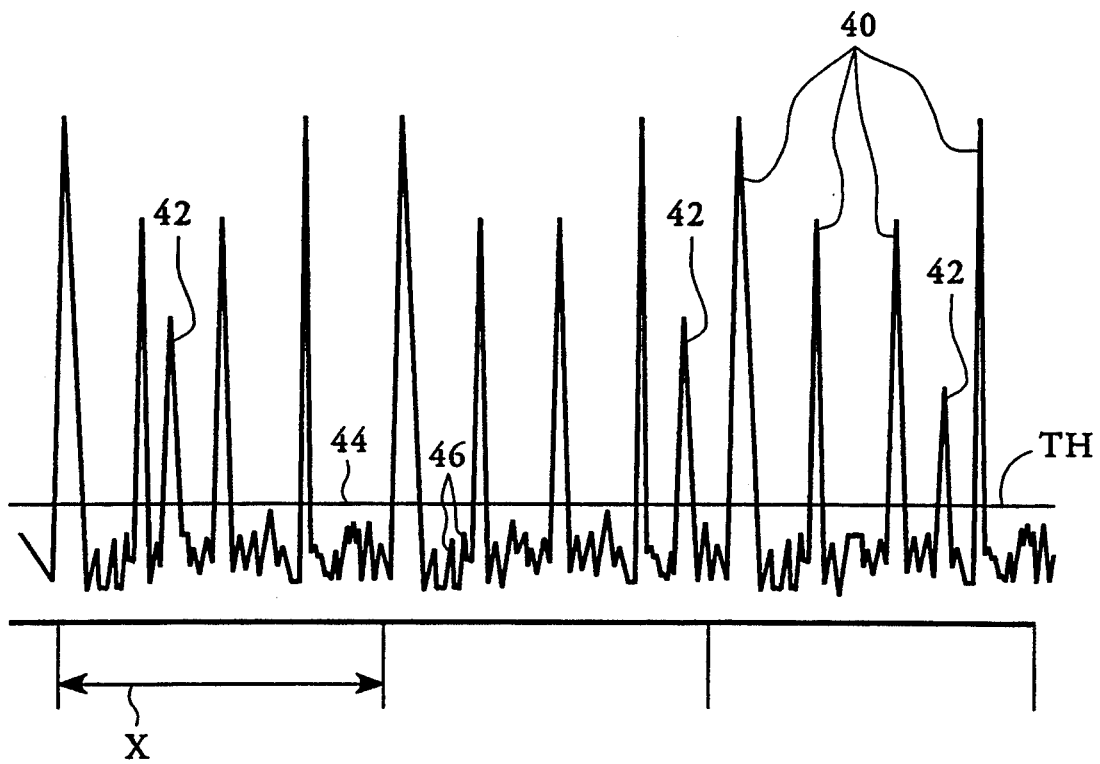
FIG. 2 is a graph of scattering intensity versus beam position obtained from scanning a patterned surface with the system of FIG. 1.

The scattered light signal is processed in order to detect particles and other defects on the semiconductor patterned wafer. In order to detect such particles and defects, it is necessary to differentiate that portion of the signal due to the particles and defects from that portion of the signal due to pattern features on the wafer. The present invention uses a periodic feature elimination technique that removes pattern features from the data based on the repetitive nature of the pattern signal. Note that the pattern signal will repeat from die to die, whereas the particle/defect signal is essentially random in nature. In FIG. 2, the scattering signal obtained from a portion of a scan line over about three die on the wafer is seen. There is an overall X periodicity to the signal, where X is the die size in the direction of the scan. A number of signal spikes 40 due to strong scattering from prominent pattern features are observed, which repeat as subsequent die are scanned. There are also a number of other signal spikes 42 that occur at irregular intervals. These random spikes 42 generally correspond to non-pattern features such as particles or defects on the inspected surface.

The scattering signal from the photodetector 26, such as a photomultiplier tube, is first amplified then converted from analog to digital form by a analog to digital converter (ADC). The conventional technique, used in prior systems, processes 8-bit digital data. An improved technique described below will use either 12-bit digital data or data that has first been converted to 12-bits by an ADC then transformed into 8-bit data according to a special transform function. The conventional technique also used a single threshold signal level for feature extraction. An improved technique described below will use multiple thresholds for different regions on a die. The conventional technique also used global or whole wafer mapping for periodic feature elimination, while an improved technique described below will use local or partial wafer mapping. Advantages of these and other improvements will become apparent as they are described.

The digital data is first processed with hardware which "featurizes" signals that are above threshold. Events above threshold are identified and kept, while events below threshold are ignored. For example, the signal spikes 40 and 42 which lie above the threshold level 44 would be kept as significant events of potential interest, while signal areas 46, which are below threshold, would be forgotten. Neighboring above-threshold events, including those from adjacent scan lines on the wafer surface, are collected together to form a "feature" of potential interest. The hardware and correlation method used to collect the adjacent events can be that described in U.S. Pat. No. 4,641,967 to Pecen. Typically, the information stored for each feature includes the location and amplitude data for at least the peak amplitude signal event and, preferably, for all of the events collected into that feature.

Figure 3:
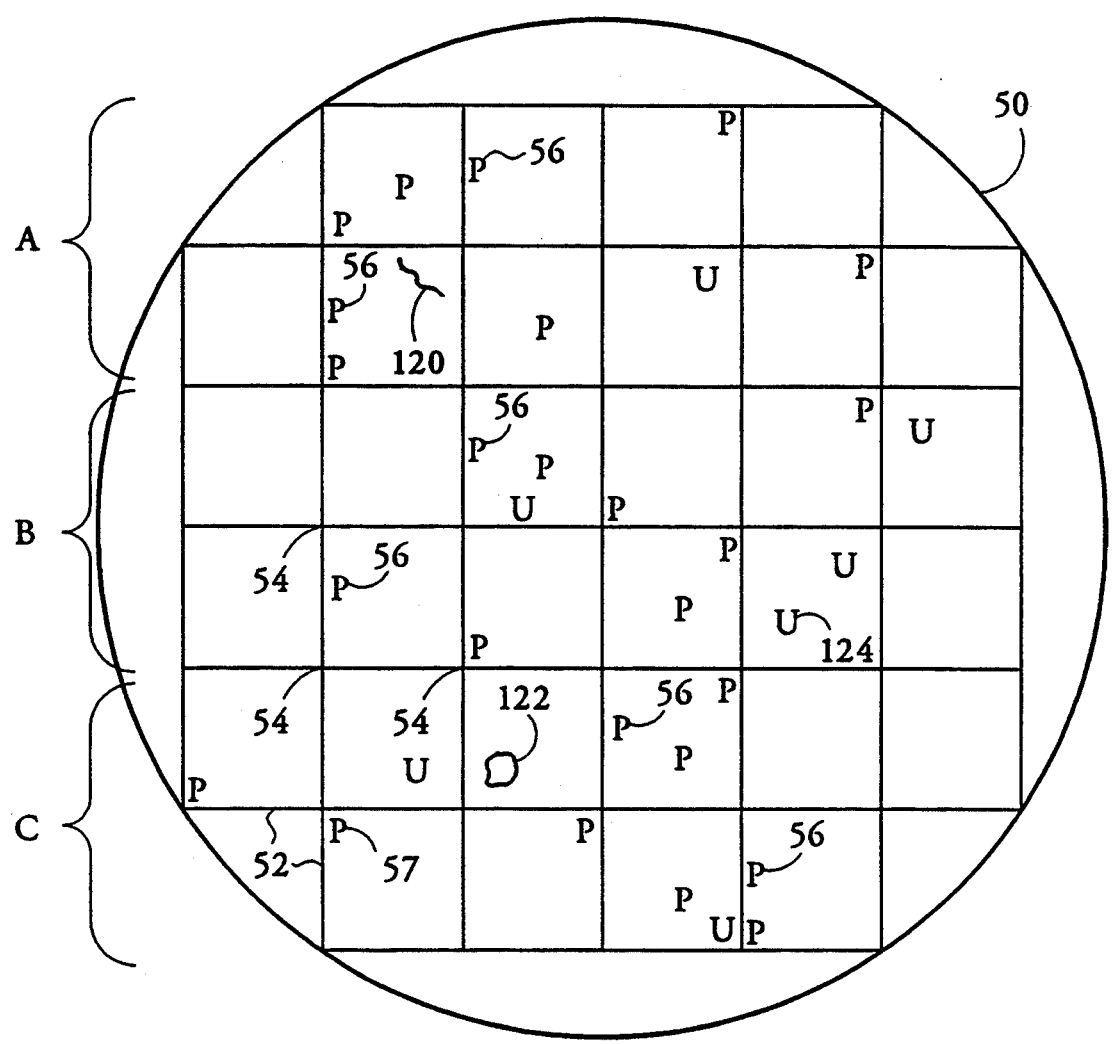
FIGS. 3 and 4 are respective maps of the surface of an entire wafer and of a single condensed die, representing data processed by the method of the present invention.

Next, the features are compared in the scan direction in order to detect sets of features that have the same X-periodicity as the die spacing. Features having a die size separation in the scan (X) direction are considered to be the same feature on different die. These features are marked or flagged as periodic or pattern features (P). Generally, only the most intense version (greatest scattering amplitude) of a periodic feature needs to be kept, while the other versions of the same feature are discarded. However, the number of corresponding features or versions in each set may be saved for use by the fuzzy logic program described below in assigning a pattern probability value. Features that do not have the same X-periodicity with any other features are marked as unique (U) and also kept. FIG. 3 shows a map or plot of the flagged features (P and U) on a wafer 50. An overlay of the die boundaries 52 is also shown. Note that after the X-periodicity comparison, only one of the periodic features (P) in each corresponding set remains in each row of die, the other versions of the same feature in that row having been discarded.

Figure 4:
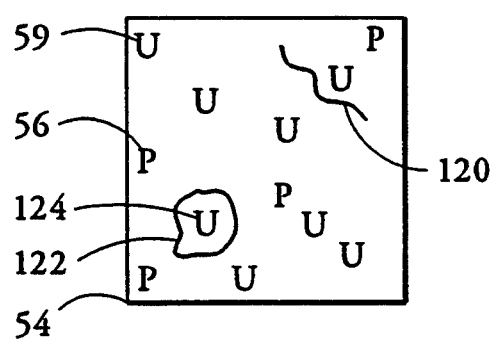

Next, the data is collapsed in the Y direction perpendicular to the scan (X) direction. (X,Y) coordinates with respect to the die origins 54 are obtained for each feature (P and U), and the features are now mapped to a single die for comparison of the features in the Y-direction. FIG. 4 shows such a die map for the features (P and U) shown in FIG. 3. Features with the same Y-periodicity as the die will overlap in the single die mapping. For example, the periodic features labeled 56 in FIG. 3 overlap in FIG. 4 and form a single periodic feature. Accordingly, the software looks for overlaps of the mapped features and applies fuzzy logic to reject those features which are likely to be pattern features. In contrast, unique features will generally not overlap and probably correspond to particles or defects on the inspected wafer. The software assigns a pattern probability value based on the number of identified features that overlap a given die coordinate. Features likely to be particles or defects are reported as such and the pattern features are discarded. Incidentally, by assigning a pattern probability value to each feature in the manner just described, the system is able to discern, after collapsing the data via the mapping technique, if a feature initially classified as periodic (the event 57 labeled P in the last row of die in FIG. 3) is instead likely to be a particle or defect and to reclassify it as unique (the event 59 labeled U in the upper left corner of the die map in FIG. 4).

Figure 5:
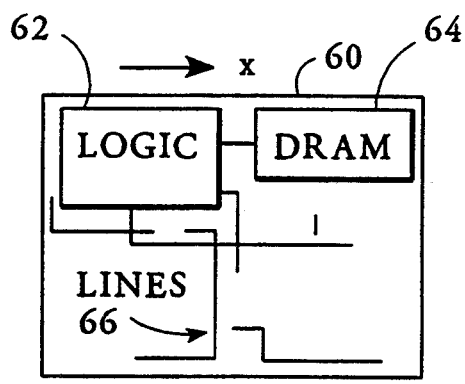
FIG. 5 and 6 and, respectively, a schematic top plan view of a representative integrated circuit die and a graph of scattering intensities obtained by scanning different regions of that die.
Figure 6:
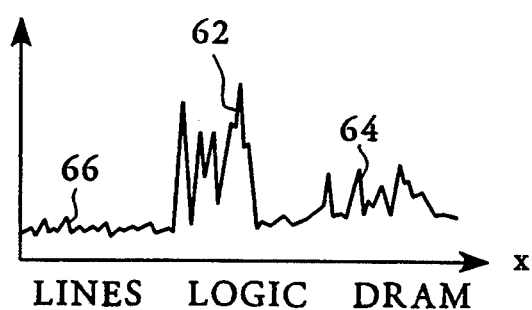

The periodic feature elimination technique, just described, allows one to detect small particle/defects in the presence of large background pattern signals and to properly reject the pattern features due to their periodic nature. At present, surface scanners use the technique with only a single threshold level for the entire wafer surface being inspected. We have discovered that using a single threshold for identifying features of potential interest in the scatter signal necessitates a trade-off between the minimum size particle or defect that can be detected and the areas of the wafer surface that can be inspected in a single beam scan. Referring to FIGS. 5 and 6, a typical integrated circuit die 60 has several different regions characterized by different levels of background scatter from the pattern on the die. For example, the circuit might include logic areas 62 with a high amount of scattering, a DRAM area 64 with a moderate amount of scattering and conductive lines 66 in areas with a relatively low amount of scattering. In many semiconductor wafers, the background signal can vary over a wide dynamic range, sometimes by as much as 1000:1 between high and low scatter regions.

Figure 7A:
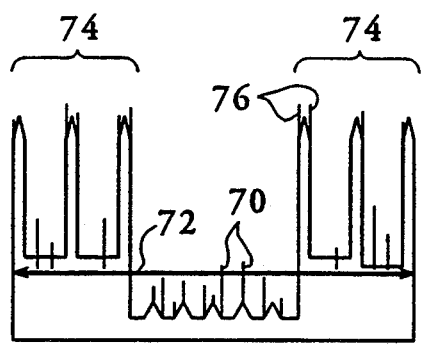
FIGS. 7a, 7b, and 7c are graphs of scattering intensity versus beam position of a patterned surface with, respectively, a single threshold of the prior art, multiple thresholds of the present invention, and local thresholds of the present invention.

With reference to FIG. 7a, in order to see the smallest particles and defects 70 on the surface, one must use a low detection threshold 72 (and increased gain) so that relatively small amounts of particle scattering will exceed the threshold. However, as seen in FIG. 7a, when the threshold 72 is set low, a large number of pattern signal 74 will also exceed the threshold, especially in the high scatter regions of the die. A problem is that any particles 76 that lie on or near a significant pattern feature on the wafer are lumped together with the pattern features and eliminated with the pattern feature. When a low threshold 72 is selected to increase sensitivity, a large fraction of the wafer 74 may be above threshold 72, leaving very little room for detecting particle features 76, and the number of particle detections may actually decrease. At best, the low threshold approach achieves its result at the cost of not being able to inspect for defects in high scatter regions of the die formed in the wafer. Alternatively, in order to be able to inspect the entire wafer, including the high scatter regions, one should increase the detection threshold level (or reduce the gain). However, this approach would result in decreased sensitivity so that many very small particles 70 in the low scatter region would be missed.

Figure 7B:
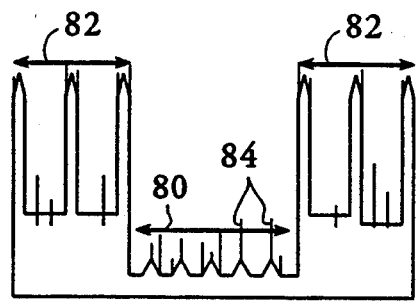

With reference to FIG. 7b, one improvement over the conventional periodic feature elimination (PFE) technique is to use separate thresholds 80 and 82 for different regions so that regions with relatively low background pattern scatter have low threshold 80 for enhanced sensitivity to small particles 84 and regions with high scatter have higher thresholds for reduced loss of inspectable wafer areas and successful detection of particles in these high scatter areas. As a result, the entire wafer, including both high and low scatter regions, can be inspected at the optimum sensitivity for the respective regions with a single scan of the wafer. Inspection regions for this multithreshold technique are any two-dimensional surface areas of a die with a unique scattering intensity compared to that of neighboring areas. The threshold for each region may be determined automatically with a learning process that uses a sample wafer identical to those to be tested. The sample wafer is inspected and the background scattering level is measured over the entire wafer. Areas with different scattering levels are demarcated. The threshold level can then be set based on the measured background signal on each distinct area. For example, the threshold could be set at a level at which a certain desired percentage of the area of a region is above that threshold. For maximum particle detection in most circumstances this percentage is in a range of from 5% to 20%. Accordingly, preferably, the level at which about 10% of the pattern signal in a given region is above the threshold is determined and used as the threshold level for that region in all subsequent wafers. Up to about 2000 different threshold levels may be selected. After customizing the thresholds for the different regions of the wafer, other wafers like the sample wafer may be inspected. The scatter signals from the separate regions are collected in a single scan of the entire wafer and then processed separately (either in sequence or in parallel) with the different assigned thresholds to identify features of interest from the above-threshold events. This method has been found to enhance particle capture by an average of about 85% over the prior single threshold method.

Figure 7C:
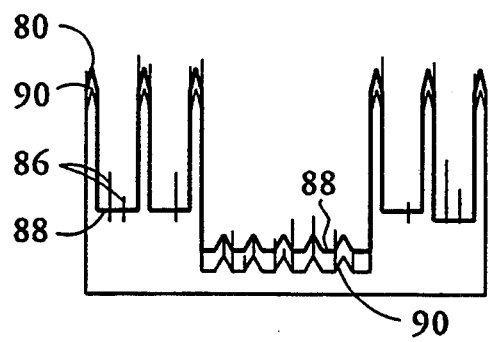

A further improvement seen in FIG. 7c extends the multithreshold concept to single pixels in the data stream. By varying the threshold 88 locally on a per pixel basis, the sensitivity to particles is maximized to the extent that even small particles 86 can be detected in local low scatter areas of a generally high scatter region. The threshold 88 is set using a sample wafer in which many identical dies can be sampled and averaged to determine local thresholds in corresponding local areas of each die. Here the threshold is set to be just above the expected pattern scattering intensity 90 for that local area.

Figure 8:
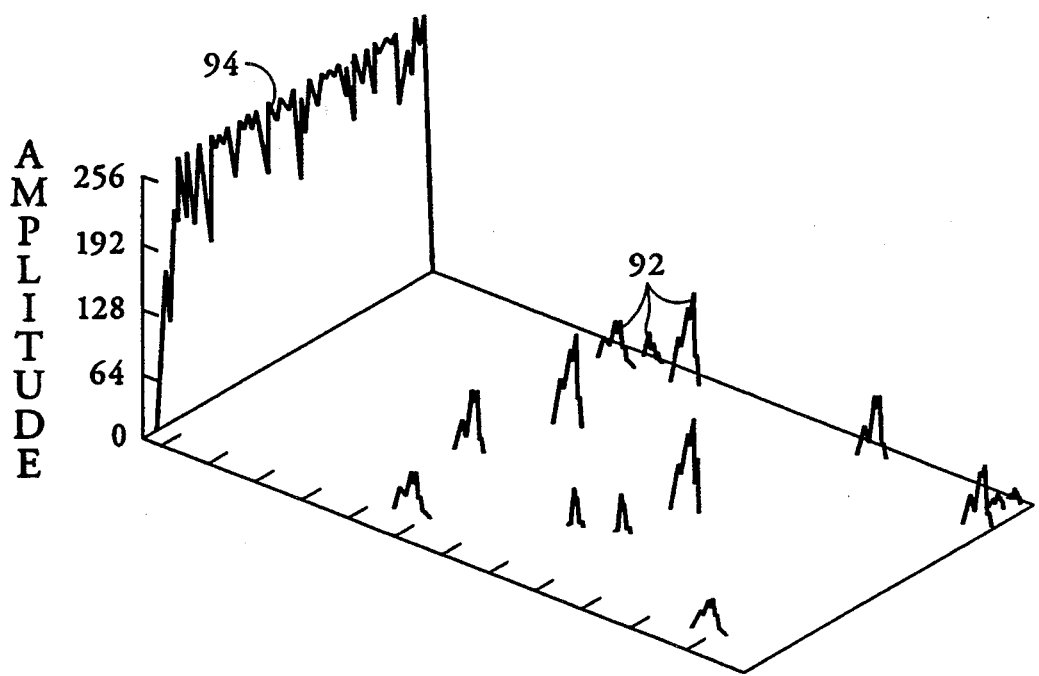
FIG. 8 is a graph of data amplitudes versus scan position of a patterned surface obtained from a low dynamic range detector of the prior art, illustrating saturation in high scatter regions.

With reference to FIG. 8, as previously noted, background scatter signals from pattern features can vary on semiconductor wafers by as much as 1000-to-1 between high and low scatter regions. Dynamic ranges on wafers of at least 200-to-1 are typical. Prior inspection systems use a detector that produces a data stream consisting of 8-bit pixels. Each pixel is capable of representing any one of 256 different scattering intensities detected by the detector. This dynamic range, while adequate for single threshold schemes where the sole question is whether or not the pixel value is above this threshold level, does not allow a multithreshold system to set meaningful thresholds over an entire wafer. When the wafer is inspected at the high gains needed to see small defects and particles 92 on the wafer, the high scatter regions on the wafer saturate the detector so that the signal levels are distorted and even clipped at the maximum level. Even if a high threshold were to be set for this region, the system would be unable to discriminate even large defects and particles against the high scatter background pattern, because the data for particles would be no different than the data for pattern. Both would be clipped at the maximum data level. Alternatively, if the gain is reduced sufficiently to avoid saturation in the high scattering regions, the resolution of the system would be insufficient to discriminate small changes in scattering intensity needed to see small particles and defects against even a low scattering background.

Figure 9:
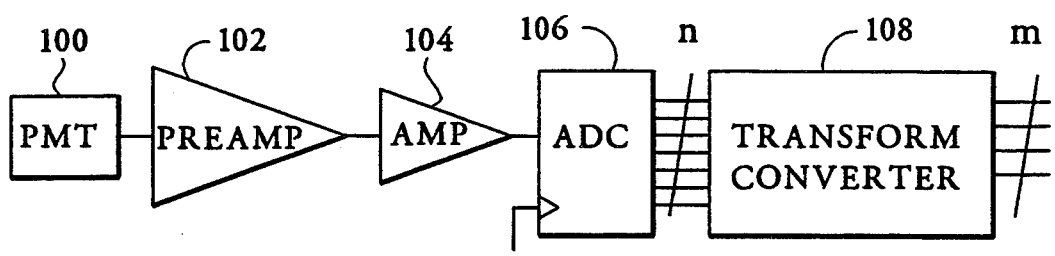
FIG. 9 is a schematic diagram of the elements of a detector of the present invention.

In FIG. 9, the present invention employs a wide dynamic range, uniform detector comprising a photomultiplier tube 100, a low noise video preamplifier/amplifier chain 102 and 104 and a high resolution analog-to-digital converter 106. The high resolution analog-to-digital converter receives the raw amplified analog scatter signal from the amplifier chain 102 and 104 and converts it to N ($>$8) bits. Preferably, a 12-bit converter is used so that the digitized data is capable of representing as many as 4096 different scattering signal levels. Alternatively, the number N of bits in the digitized data pixels could be 16 or some other number greater than 8. This high resolution detector extends the dynamic range of the system, allowing collection of scattering data from the surface under test with maximum sensitivity for low scatter regions of the wafer surface, while ensuring that the signal does not saturate in the high scatter regions. Instead of being clipped off at the maximum data level, as in the 8-bit, 256-level system, the high scatter regions have background pattern signal levels near 3000 in the 12-bit, 4096-level system, leaving room for the discrimination of the even larger signal levels from particles and defects against this background. The wide dynamic range thus makes the multiple threshold technique work much more effectively, since one can still detect differences in scattering levels in the high scatter regions.

The higher resolution detector could also be used to enhance detection of particles and defects actually on a surface relative to noise in the scattering signal. The high resolution enables the system to better discern the shape of a potential feature of interest, represented by the aspect ratio of the scattering signal for that feature that is above a certain threshold. Features that have aspect ratios that are different from the scanning beams are likely to be noise or due to structures on the substrate, whereas features that have substantially the same aspect ratio as the beam are likely to be real. Use of this distinction can reduce noise and false counts by the system. This technique could also be used with bare (as opposed to patterned) substrates.

Figure 10:
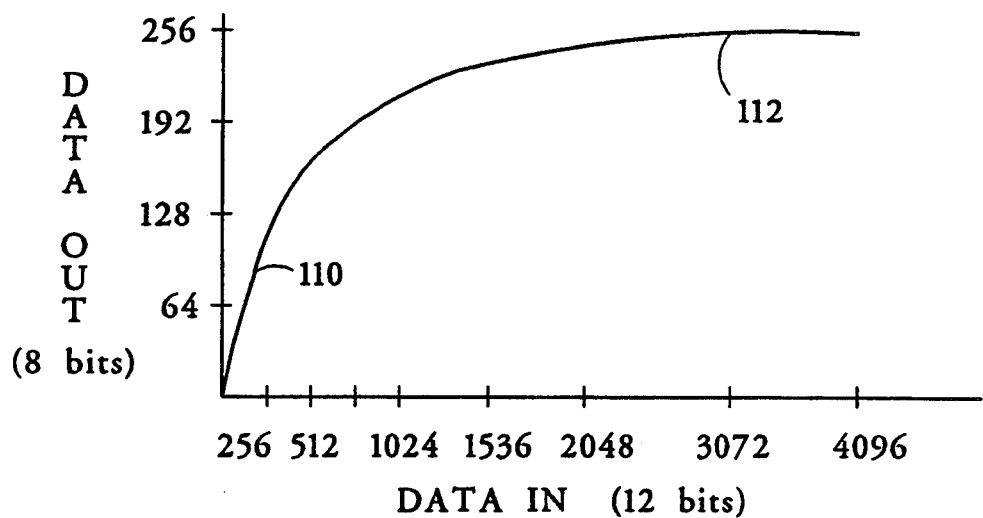
FIG. 10 is a graph of a transform function in terms of 8-bit data out versus 12-bit data in carried out by the transform converter in the detector of FIG. 9.
Figure 11:
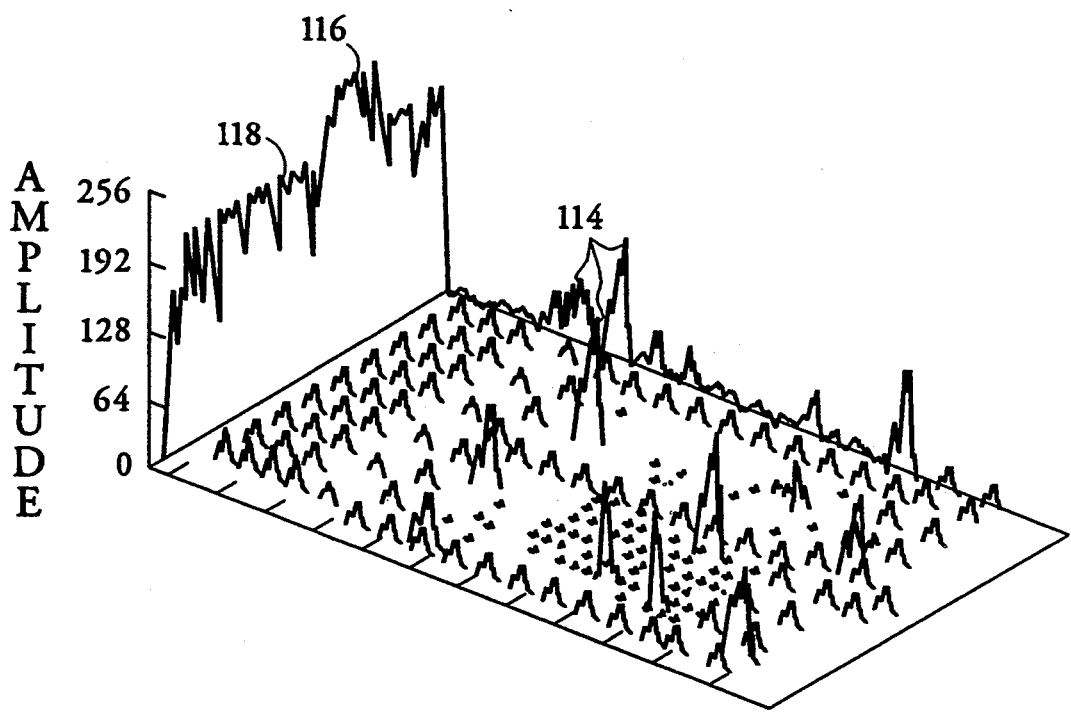
FIG. 11 is a graph of data amplitudes versus seen position of a patterned surface obtained from the high dynamic range detector of FIG. 9 with the transform function conversion of FIG. 10.

The wide dynamic range detector may also include a transform converter or data compressor 108 to transform or convert the high resolution 12-bit data in a nonlinear manner back into 8 bits in order to fit existing software data structures as a backwards compatibility convenience, while still providing the full benefit of wide dynamic range handling of the primary data by the detector hardware. The nonlinear transform function is selected to provide varying sensitivity for different subranges of the overall signal range in order to optimize the resolution needed in each subrange. In most applications, it is desirable to use a function that has a steep response 110 at the low end of the signal range and a reduced response 112 at the high end, as seen in FIG. 10. Preferably, the transform function is a logarithmic function. This logarithmic function converts 12-bit data in scattering intensity units into an 8-bit scale that is approximately linear with the diameters or sizes of the scattering particles or defects (for particles and defects less than 1 $\mu$m size). Also, the same percentage change in signal level in the raw data results in a uniform difference in levels in the converted data. However, other nonlinear transform functions could also be used. The result of using high resolution data collection followed by a logarithmic transformation to an 8-bit data stream is seen in FIG. 11. In comparison with the prior low resolution data collection results in FIG. 8, the features 114 in the low scattering areas are more prominent and particles 116 can now be observed against the pattern background signal in the high scattering regions.

The transform converter 108 may be implemented as a lookup table. The lookup table can be a read-only memory or a memory that is software programmable from a central processing unit. The 12-bit input value is the address of an 8-bit memory location that contains the transformed value as its stored entry. Other means for carrying out the transform function could also be used.

The data may also be calibrated to correct for spatial nonuniformities in the system, principally optical in nature, that repeat across the measurement system. Such nonuniformities cause a variable response as a function of position across the wafer substrate under inspection. This variable response results in unpredictable periodic feature elimination (PFE) across the wafer in which some marginal pattern features that are just above threshold fail to be filtered out by the PFE technique and end up being treated as particles, thereby producing false particle counts. Thus, there is a need to correct the data with a calibration scheme that normalizes the peaks based on their position on the wafer surface. This data correction may be implemented in hardware at the front end using the same lookup table memory 108 as that used for the transform conversion. In particular, the transform lookup table can be implemented as a series of memory banks, which can be read-only memory or memory that is software programmable from a central processing unit or downloaded from a system hard disk, where each memory bank represents the correction table for a given range of X locations (in the beam scanning direction) on the wafer. Data from a given range of X addresses specifies a unique bank of memory and each 8-bit memory location in this particular bank of memory is accessed by the uncorrected 12-bit valve for that location. The content of the accessed memory location is the transformed and corrected data for that scattering level and range of X locations.

The correction factor for each bank of memory may be determined using a calibration wafer for reference. The calibration wafer typically contains a uniform distribution of scatterers that are known to be identical. By scanning this calibration wafer with the system, any spatial variation in the scatter response across the wafer can be measured. From this measured response, the wafer can be broken into a set of blocks representing specified ranges of X locations and mapping to unique memory banks and correction factors can be calculated for each block. Then correction factors can be stored in a system hard disk from which it can be downloaded to the respective memory banks of the lookup table. Alternatively, correction of spatial scattering variations can also be done simultaneously with the inspection of a wafer surface, using a calibration tile adjacent to the wafer under inspection for in situ measurement. Thus, the measurements and data correction could be carried out in situ as the actual inspection is carried out.

Referring again to FIGS. 3 and 4, the periodic feature elimination (PFE) software maps all of the die on an entire wafer to a single die and looks for overlapping features. This technique works fine when the particle/defect density is low. However, as the number of particle and other features increases, the software quickly runs out of space on the die map (FIG. 4) to put additional features. As the defect density increases, the accidental overlap of random events becomes more likely. These random data collisions increase the probability that particles and other defects will be eliminated with the pattern features, lowering the capture rate for particles and other defects. In general, it has been found that capture rate begins to fall off significantly as the number of random features increases from 200 to 500 events per wafer. Another problems is that occasionally wafers will get a scratch 120 or a large number of defects 122 on one die from a blowout or particle shower. When mapped to the single die (FIG. 4), the scratch 120 or blowout 122 masks out other defects 124 in the same location of the die over the entire wafer.

Figure 12A:
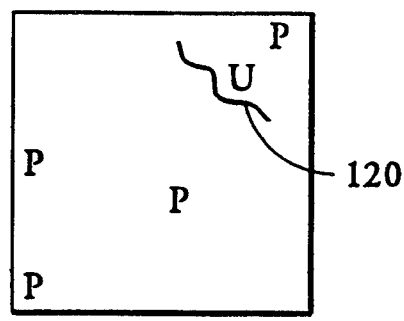
FIGS. 12a–12c are maps of condensed die, similar to FIG. 4, corresponding to respective subwafer regions A, B and C in FIG. 3.
Figure 12B:
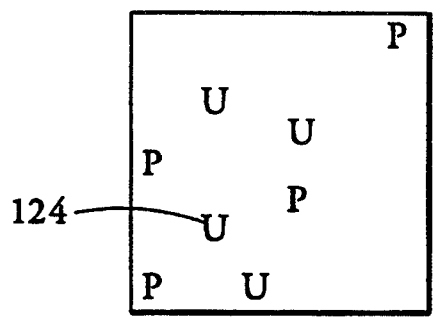
Figure 12C:
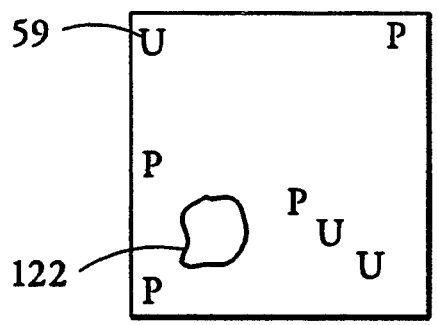

An improved "local" PFE technique of the present invention enhances the PFE technique for use when the defect density is high. The local PFE technique modifies the prior global PFE technique such that the periodicity comparison is limited to only a local region or neighborhood of die on the wafer being inspected, instead of comparing all of the die on the wafer. Now, instead of mapping the entire wafer 50 in FIG. 3 to a single die (FIG. 4), the local PFE software maps subwafer regions to a die, so that there are fewer data collisions. For example, the wafer 50 in FIG. 3 may be divided into the subwafer regions labeled A, B and C, each consisting of two rows of die. Thus, subwafer region A consists of the first two rows of die in FIG. 3, subwafer region B consists of the next two rows of die and subwafer region C consists of the last two rows of die. Then, each subwafer region A, B and C is separately mapped to die maps shown in FIGS. 12a, 12b and 12c, respectively. The map in FIG. 12a identifies the periodic (P) and unique (U) feature forms in the first two rows of the wafer of FIG. 3, including the scratch 120, by looking for overlapping features as in the prior PFE technique. However, the scratch 120 is no longer able to obscure features in the same die position on the other die maps in FIGS. 12b and 12c. Likewise, the maps in FIGS. 12b and 12c identify the periodic (P) and unique (U) features found in the die of their respective subwafer regions B and C in FIG. 3. Blowout events 122 occurring in one subwafer region C and mapped to the die map in FIG. 12c will not obscure features 124 in another subwafer region B, because these features are mapped to a different die map (FIG. 12b). The pattern probability software continues to classify pattern (P) and particle and defect (U) features based on their recurrence, as before, but based now only on the die within a given subwafer region A, B or C. Some features initially identified as periodic (P) in the X (scan direction) comparison, as feature 57 in FIG. 3, may be redesignated as probably a particle or defect, as feature 59 in FIG. 12c, by the software.

Typically, about 10% of a wafer surface, equivalent to about 2 rows of die or 30 dies worth of data, are mapped as a local area or subwafer to a die map at a time. The extent of the local region is preferably controllable by the user based on the anticipated particle/defect density of the particular surfaces to be inspected. The local region could range from just two die for extremely high defect densities to an entire wafer, as in the global PFE technique for low densities. With the typical local area of about 10% of a wafer, there is a factor of about 3 to 10 improvement in the number of particles and defects than can be counted with the capture rate not falling off significantly until the defect density reaches about 1500 to 2000 events per wafer. Thus, by reducing the probability of accidental overlay of defects and particles when testing for die-to-die periodicity, one can greatly increase the capture rate, allowing surfaces with higher defect densities to be inspected.

The local PFE technique also reduces the loss of inspection in areas of the die that correspond to blowouts and scratches to only the local region containing the blowout. Defect masking now applies only to the local region containing the blowout or scratch. Other local regions are unaffected, so that corresponding die areas can be inspected for particles and defects in those other local regions. The local PFE technique also improves the die-to-die alignment tolerance, since comparisons between die are only made locally. Processing time is also reduced, since the overall number of comparisons is reduced.

The improvements in the periodic feature elimination process, including use of multiple thresholds in different scattering areas, the use of a high resolution, wide dynamic range detector, possibly including nonlinear transform function conversion of the data and spatial nonuniformity correct, and the use of local die comparisons in place of an entire wafer, result in increased particle and defect detection without requiring additional scans of the wafer and slower inspection throughput.

We claim:

1. A method of detecting particles and defects on a periodically patterned surface, comprising scanning a periodically patterned surface with a light beam and detecting light scattered from said surface to produce an electrical signal that is a measure of the detected intensity of light scattered from each position on said surface that is scanned by said light beam, said surface having both periodically recurring pattern features and randomly occurring particle and defect features thereon, said surface having a plurality of regions characterized by different background scattering intensities, assigning a threshold intensity level to each of said plurality of regions, regions with higher background scattering intensities being assigned higher threshold intensity levels than regions with lower background scattering intensities, identifying from said electrical signal those features that have a detected scattering intensity which is greater than the threshold intensity levels assigned to the specific regions of said surface containing the respective features, and storing at least the locations of said identified features, and comparing said locations of said identified features to remove those features that periodically recur, features remaining after said comparison and removal of said periodic features being identified as said randomly occurring particle and defect features on said surface.

2. The method of claim 1 wherein assigning a threshold intensity level to each of said plurality of regions characterized by different background scattering intensities comprises scanning a reference wafer having the same periodically recurring pattern features as said periodically patterned surface and measuring said background scattering intensity for each scan position, forming regions from adjacent scan positions such that scan positions within each region have substantially similar background scattering intensity levels, and selecting a threshold intensity level for each region which is above the characteristic background scattering intensity for that region, different regions with substantially different characteristic background scattering intensities being assigned substantially different threshold intensity levels.

3. The method of claim 2 wherein said threshold intensity levels are selected such that a specified percentage of scan positions with each region have background scattering intensity levels above said threshold intensity level for that region.

4. The method of claim 3 wherein said specified percentage is in a range from 5% to 20%.

5. The method of claim 1 wherein each region assigned a threshold intensity level corresponds to a single pixel of scattering data obtained from said electrical signal such that a different threshold intensity level is assigned to each single-pixel region.

6. The method of claim 1 wherein producing said electrical signal that is a measure of the detected intensity of scattered light includes converting an analog electrical signal to a high resolution digital data stream such that a smallest feature of interest is resolvable in said data stream against background scattering and such that a maximum detected scattering intensity is resolvable in said data stream against lesser scattering intensities.

7. The method of claim 6 wherein said digital data stream comprises a 12-bit pixel for each position on said surface that is scanned by said light beam.

8. The method of claim 7 wherein said 12-bit pixels are nonlinearly transformed to 8-bit pixels by a transform converter executing a specified digital nonlinear transform function.

9. The method of claim 8 wherein said nonlinear transform function has a steep response for low 12-bit pixel values and a reduced response for high 12-bit pixel values.

10. The method of claim 9 wherein said transform function is a logarithmic function.

11. The method of claim 8 wherein said transform converter executing said transform function is a lookup table memory addressed by said 12-bit pixels and storing 8-bit pixel values at corresponding addresses read by said 12-bit pixels.

12. The method of claim 6 further comprising measuring an aspect ratio characterizing each feature identified from said electrical signal, comparing said aspect ratio for each identified feature with an aspect ratio characteristic of said scanning beam, and identifying features with aspect ratios that are substantially different from said scanning beam as noise and features with aspect ratios that are substantially the same as said scanning beam as real features of said surface.

13. The method of claim 1 wherein comparing said locations of said identified features includes mapping features from a plurality of periodically repeating die on said surface to a single die map, positions of said features relative to said die on said surface corresponding to map positions of said features on said single die map, and identifying overlapping features on said die map as periodic features and unique features on said die map as particle and defect features.

14. The method of claim 13 wherein features from the entire surface are mapped to said single die map.

15. The method of claim 13 wherein features from only a portion of said surface are mapped to said single die map, other portions being mapped to other die maps.

16. A method of detecting particles and defects on a periodically patterned surface, comprising scanning a surface with a light beam and detecting light scattered from said surface with a wide dynamic range detector, said surface having both pattern features and particle and defect features thereon in regions of substantially differing background scatter levels, said wide dynamic range detector producing a high resolution digital data stream in which the smallest particle and defect feature of interest is resolvable in said data stream against said background scatter in relatively low scatter regions and in which a maximum detected scattering intensity is resolvable in said data stream from lower detected scattering intensities, and identifying from said digital data stream locations of particle and defect features on said surface.

17. The method of claim 16 wherein said digital data stream produced by said wide dynamic range detector comprises 12-bit pixels, each representing one of 4096 resolvable detected scattering intensities at a location scanned by said beam.

18. The method of claim 17 wherein said 12-bit pixels in said digital data stream are converted to 8-bit pixels by a transform converter executing a nonlinear transform function.

19. The method of claim 18 wherein said transform function has a relatively steep response for low 12-bit pixel values and a reduced response for high 12-bit pixel values.

20. The method of claim 19 wherein said transform function executed by said transform converter is a logarithmic function.

21. The method of claim 18 wherein said transform converter converting said 12-bit pixels to 8-bit pixels is a memory lookup table addressed by said 12-bit pixels and storing 8-bit pixel values at locations accessed by said 12-bit pixels.

22. The method of claim 16 wherein said digital data stream representing detected scattering intensities is adjusted with correction factors according to scan position on said surface to correct for spatial nonuniformities.

23. The method of claim 22 wherein said correction factors are derived by scanning a calibration wafer with a uniform distribution of substantially identical scatterers, detecting light scattered from said calibration wafer, and calculating scattering response across said calibration wafer.

24. The method of claim 23 wherein said calibration wafer is positioned adjacent to said surface and scanning of said calibration wafer and derivation of said correction factors is done simultaneously with scanning of said surface.

25. The method of claim 16 further comprising measuring an aspect ratio characterizing each feature identified in said digital data stream, comparing said aspect ratio for each identified feature with an aspect ratio characteristic of said scanning beam, and identifying features with aspect ratios that are substantially different from said scanning beam as noise and features with aspect ratios that are substantially the same as said scanning beam as real features of said surface.

26. The method of claim 16 wherein identifying said locations of particle and defect features includes assigning higher threshold intensity levels to relatively high background scatter regions of said surface and lower threshold intensity levels to relatively low background scatter regions of said surface and identifying features in said data stream that exceed the assigned threshold intensity level for the corresponding region being scanned.

27. The method of claim 26 wherein each individual pixel in said data stream is assigned a separate threshold intensity level.

28. The method of claim 26 wherein features exceeding said threshold are mapped from a plurality of periodically repeating die on said surface to corresponding locations on a single die map, and overlapping features on said map are removed from said map, unique features being identified as particle and defect features on said surface.

29. The method of claim 28 wherein said plurality of die with features in said data stream mapped to said single die map are only a portion of all die on said surface.

* * * * *